(12) United States Patent
Cheng et al.

(10) Patent No.: US 8,304,000 B2
(45) Date of Patent: *Nov. 6, 2012

(54) PROCESS FOR PREPARING WATER EXTRACT OF CINNAMON

(75) Inventors: Nanzheng Cheng, Foster City, CA (US); Long Luo, Beijing (CN); Jiang Kong, Beijing (CN)

(73) Assignee: Beijing Tang-An Nutrition & Healthcare Products Co. Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/252,958

(22) Filed: Oct. 4, 2011

(65) Prior Publication Data

US 2012/0128804 A1 May 24, 2012

Related U.S. Application Data

(63) Continuation of application No. 12/952,898, filed on Nov. 23, 2010.

(51) Int. Cl.
*A61K 36/54* (2006.01)
(52) U.S. Cl. ...................................... 424/739
(58) Field of Classification Search .................. None
See application file for complete search history.

(56) References Cited

U.S. PATENT DOCUMENTS

| | | | |
|---|---|---|---|
| 6,200,569 B1 | 3/2001 | Cheng et al. | |
| 2006/0013903 A1* | 1/2006 | Romero et al. | 424/739 |
| 2007/0196520 A1 | 8/2007 | Lin et al. | |

FOREIGN PATENT DOCUMENTS

| | | | |
|---|---|---|---|
| CN | 1133877 | | 10/1996 |
| CN | 1133877 A | * | 10/1996 |

OTHER PUBLICATIONS

Small. Culinary Herbs. NRC Research Press. 2006. p. 28.*
Carbwars.com. Retrieved from the internet. <http://carbwars.blogspot.com/2008/01/cinnamon-warning.html>. Retrieved on Dec. 16, 2011. 3 Pages.*
Herrero et al. Sub- and Supercritical Fluid Extraction of Functional Ingredients From Different Natural Sources: Plants, Food-Byproducts, Algae and Microalgae. 2006. pp. 1-34.*
Macquer et al. Elements of the Theory and Practice of Chymistry. vol. 2. 1758. pp. 128-129.*
Fox. The Spatula. vol. 11. The Spatula Publishing Co. p. 12.*
Miller et al. Biotechnology and Bioengineering. vol. X. 1968. pp. 684-688.*
Jia, Q., Liu, X., Wu, X., Wang, R., Hu, X., Li, Y., and Huang, C., (2009). Hypoglycemic activity of a polyphenolic oligomer-rich extract of *Cinnamomum parthenoxylon* bark in normal and streptozotocin-induced diabetic rats. Elsevier, Phytomedicine, ScienceDirect, pp. 744-750 2009.
Mang, B., Wolters, M., Schmitt, B., Kelb, K., Lichtinghagen, R., Stichtenoth, D.O., and Hahn, A. Effects of a cinnamon extract on plasma glucose, $HbA_{1c}$, and serum lipids in diabetes mellitus type 2. (2006). European Journal of Clinical Investigation, pp. 340-344 2006.
Kim, Sung Hee, Hyun, Sun Hee, and Choung, Se Young., (2006). Anti-diabetic effect of cinnamon extract on blood glucose in db/db mice. Elsevier, Journal of Ethno-Pharmacology, ScienceDirect, pp. 119-123 2006.
Khan, Alam, Bryden Noella A., Polansky, Marilyn M., and Anderson, Richard A., (1990). Insulin Potentiating Factor and Chromium Content of Selected Foods and Spices. Biological Trace Element Research, vol. 24, pp. 183-188, 1990.
Anderson, Richard A., Broadhurst, C. Leigh, Polansky, Marilyn M., Schmidt, Walter F., Khan, Alam, Flanagan, Vincent P., Schoene, Norberta W., and Graves, Donald J. (2004). Isolation and Characterization of Polyphenol Type-A Polymers from Cinnamon with Insulin-like Biological Activity. J. Agric. Food Chem pp. 65-70 2004.
Consumers, who eat a lot of cinnamon, currently have an overly high exposure to coumarin. BfR Health Assessment No. 043/2006, pp. 1-13 Jun. 16, 2006.
International Search Report mailed Feb. 23, 2012 for PCT/CN2011/082322.

* cited by examiner

*Primary Examiner* — Melenie McCormick
(74) *Attorney, Agent, or Firm* — Perkins Coie LLP.

(57) ABSTRACT

This invention relates to an improved process for preparing water extract of cinnamon in a large scale. The process comprises the steps of: (a) adding an aqueous solvent such as water to at least 5 kg of a cinnamon raw material at a water to material ratio of 1:1 to 100:1, (b) boiling the mixture of (a) for at least 5 minutes, (c) removing the solid debris from the mixture, (d) storing the liquid portion of the mixture at about −5 to 25° C., preferably 0-10° C., until a top layer of oil is formed and partitioned, (e) removing the top layer of oil, and (f) collecting the remaining liquid portion. The present process prepares a cinnamon water extract product with a minimal content of potentially toxic cinnamaldehyde and coumarin, while increasing the contents of the active ingredients of polyphenolic polymers for controlling blood glucose level.

19 Claims, No Drawings

PROCESS FOR PREPARING WATER EXTRACT OF CINNAMON

This application is a continuation application of U.S. application Ser. No. 12/952,898, filed Nov. 23, 2010; the content of which is incorporated herein by reference in its entirety.

TECHNICAL FIELD

This invention relates to an improved process for preparing water extract of cinnamon in a large scale. The improved process includes a step of storing the material at a cold temperature to partition the oil layer from the remaining aqueous solution. The improved process reduces the potentially toxic cinnamaldehyde contents in the final product, while maintaining or increasing the contents of the active ingredients of cinnamon for controlling blood glucose levels.

BACKGROUND OF THE INVENTION

Diabetes mellitus is a major public health problem. In the United States, there are over 10 million patients with diabetes. Diabetes is a syndrome that is caused by a relative or an absolute lack of insulin. Clinically, it is characterized by symptomatic glucose intolerance as well as alterations in lipid and protein metabolism. The maintenance of normal blood sugar levels is achieved by the actions of several hormones, most notably insulin, but also glucagon, epinephrine, corticosteroids, and growth hormone. Hypoglycemia, or low blood sugar, is characterized by below normal levels of blood glucose. On the other hand, hyperglycemia is exemplified by higher than normal concentrations of glucose in the blood. The pancreas produces insulin which is released in response to increased blood glucose concentrations. Insulin works to lower the blood sugar level by stimulating the uptake of glucose by cells. Glucose is used in cellular metabolism to produce energy, or is converted to glycogen for storage in the liver and muscles, or is used in the production of triglycerides and fats.

Water extracts of cinnamon exhibit an insulin potentiating activity, i.e. they increase apparent insulin activity as measured by increased glucose uptake by cells (U.S. Pat. No. 6,200,569). Improved insulin activity leads to decreased circulating insulin, which leads to lower blood glucose and lower glycosylated hemoglobin levels in patients; it also has an effect on smoothing out fluctuations in glucose levels. In the '569 patent, water extracts were prepared by extracting cinnamon plants with water, removing the solid debris, and collecting the liquid extracts. The liquid extracts could be used directly or dried to a powder form.

Mang et al (*European J. Clin. Invest.* 36:340-344, 2006) report that diabetes mellitus type 2 patients treated with 3 g of cinnamon water extract powder per day for 4 months decreased fasting plasma glucose level, in comparison with placebo-treated patients.

Anderson et al (J. Agric. Food Chem. 52:65-70, 2004) report the isolation and characterization of polyphenol type-A polymers from cinnamon. Two trimers with a molecular mass of 864 and a tetramer with a mass of 1152 were isolated. These polymers are water-soluble and are believed to be the active ingredients of cinnamon that potentiate insulin action and control glucose metabolism.

Cinnamon is composed of between 1-8% of essential oils, in which 65-90% is cinnamaldehyde. (BfR (Bundesinstitut für Risikobewertung) Health Assessment No. 044/2006, Aug. 18, 2006). He et al (*J. Agric Food Chem.* 53:2424-2428, 2005) found that in 1 g of *cassia* cinnamon (raw material), cinnamaldehyde level was between 13.1 and 56.9 mg (mean 28.9 mg). Cinnamaldehyde is a yellowish oily liquid and solidifies at −7.5° C. (Merck Index).

Lewis et al. (*Environ Health Perspect* 104:1011-1016, 1996)) report that cinnamaldehyde was tested positive for potential carcinogenicity in the COMPACT evaluation.

The chemical name of coumarin is 1-benzopyran-2-one (CAS Number: 91-64-5). Coumarin is poorly soluble in water but readily soluble in alcohol. Coumarin is a naturally occurring flavoring substance which is contained in many plants such as woodruff, sweet clover, Tonka beans. Higher concentrations can be found particularly in some types of cinnamon. Large amounts of coumarin can cause hepatic damage—coumarin may only be used as an ingredient of flavorings and other food additives with flavoring properties in the food sector. In animal experiments, coumarin can trigger the formation of tumors. (see BfR Health Assessment No. 043/2006, 16 Jun. 2006) Coumarin is not as potentially toxic as cinnamaldehyde. Still, it is undesirable to have large amounts of coumarin for human consumption.

There exists a need for an improved process to prepare water extract of cinnamon. The improved process reduces the contents of potentially toxic cinnamaldehyde and coumarin in the final product, while maintaining or increasing the active ingredients of cinnamon.

SUMMARY OF INVENTION

This invention is directed to an improved process for preparing water extract of cinnamon in a large scale. The process comprises the steps of: (a) adding an aqueous solvent such as water to a cinnamon raw material at a solvent to material ratio of 1:1 to 100:1 (w/w), (b) boiling the mixture for at least 5 minutes, (c) removing the solid debris from the mixture to obtain a liquid portion, (d) storing the liquid portion of the mixture at −5 to 25° C. until a top oil layer is formed and partitioned, (e) removing the top oil layer, and (f) collecting the remaining liquid portion. After the step (f), the process optionally comprises a step (g) of centrifuging the remaining liquid portion with a tubular centrifuge to remove solids of less than 1 micron and collect the supernatant.

The present process is suitable for processing 5-5,000 Kg of a cinnamon raw material. The present process prepares a cinnamon water extract product with a reduced amount of potentially toxic cinnamaldehyde, while increasing the contents of the active ingredients of polyphenolic polymers for controlling blood glucose level.

DETAILED DESCRIPTION OF THE INVENTION

The present invention relates to an improved process for preparing cinnamon water extract. The inventors have discovered that by storing the liquid water extract of cinnamon at a cold temperature (−5 to 25° C., preferably 0-10° C.), a layer of oil is formed and separated from the remaining aqueous portion. By removing the oil layer, the cinnamaldehyde content in the final product is reduced, whereas the contents of the active ingredients that are effective to potential insulin activity and to lower blood glucose level are increased.

The process of the present invention comprises the steps of: (a) adding an aqueous solvent such as water to a cinnamon raw material at a water to material ratio of 1:1 to 100:1 (w/w), (b) boiling the mixture for at least 5 minutes, (c) removing the solid debris from the mixture to obtain a liquid portion, (d) storing the liquid portion of the mixture at −5 to 25° C. until a top oil layer is formed and partitioned, (e) removing the top oil layer, and (f) collecting the remaining liquid portion.

After the step (f), the process optionally comprises a step (g) of centrifuging the remaining liquid portion with a tubular centrifuge to remove small solids and collect the supernatant. The supernatant is optionally dried to obtain the cinnamon water extract in a dry powder form.

Alternatively, after step (f), the process optionally comprises a step of drying the liquid portion of (f) to obtain the cinnamon water extract in a dry powder form.

The process of the present invention is particularly suitable for a large scale production. Large scale, as used herein, refers to the starting material of about ≧5 Kg or ≧10 Kg, preferably ≧50 Kg, preferably ≧100 Kg, more preferably ≧500 Kg, and most preferably ≧1000 Kg. The present invention is suitable for processing a starting material, for example, in the range of about 5-2,000 Kg, 10-2,000 Kg, 10-5,000 Kg, 50-2,000 Kg, 50-5,000 Kg, 100-2,000 Kg, 100-5,000 Kg, 400-2,000 Kg, 400-5,000 Kg, 1,000-5,000 Kg, or 1,000-10,000 Kg.

"About" as used in this application, refers to ±15% of the recited value.

Preferred source of a raw material of cinnamon is bark from a cinnamon tree, in the family of Cinnamomum. Preferred species are *Cinnamomum mairei, Cinnamomum zeylanicum, Cinnamomum burmannii,* and *Cinnamomum cassia. Cinnamomum mairei* is a tree with highly aromatic bark, which bark can be used for preparing extracts. Commercial cinnamon bark, which is the dried inner bark of the shoots, and ground cinnamon obtained from a grocery store can also be used for preparing extracts.

In the process step (a), the cinnamon raw material is obtained either as a ground powder or is prepared by cutting the plant into small pieces, pulverizing it, grinding it or otherwise increasing the surface area of the pieces of tissue to facilitate extraction.

In the process step (a), aqueous hydrophilic solvents are used for extraction of active ingredients that have insulin potential activity. Because it is safe, easy to use, and economic, water (de-ionized water, distill water, purified water, or tap water) is a preferred solvent for extraction. In addition, water does not extract those impurities soluble only in acid or base. A small amount of buffer can be added to the water to maintain the pH. A small amount of acid, base, ethanol, or methanol also can be added to the distilled water as a solvent for extraction. However, high concentrations, such as 50%, of ethanol can extract undesired organic impurities such as cinnamaldehyde, which is toxic when present in large amounts for human consumption. In the process step (a), the aqueous solvent to the raw material ratio is about 1:1, or 2:1, or 5:1, or 10:1, or 20:1, or 30:1, or 100:1 (w/w); or any range in between the above recited ratios.

In the process step (b), the water/raw material mixture is boiled for at least 5 minutes, or 10 minutes, or 30 minutes, or an hour, or 2 hours, or 4 hours, or 6 hours, or 8 hours, or 10 hours, or any range in between the above recited time. The desired boiling time depends on the amount of the raw material and water. The desired boiling time for a large amount of raw materials is longer than that for a small amount of raw materials. The process steps (a)-(c) can optionally be repeated several times, e.g., 2-8 times, or 2-4 times. After each boiling step, the supernatant is removed and collected, and new water is added to the solid material, and the mixture is boiled. After the boiling steps are completed, the supernatants are combined.

In the process step of (c), the liquid portion is separated from the solid debris by centrifugation, filtration, or decanting. The solid debris is discarded, and the liquid portion is collected.

The liquid portion is optionally concentrated to a smaller volume for convenient handling. Typically, the liquid portion is concentrated by 5-50 folds, and the volume is typically reduced to less than 1000 L. The concentration can be carried out by any means, for example, evaporation, vacuum evaporation, or other means known to a skilled person for concentration of a liquid material.

Then the liquid portion is stored at a cold temperature for a sufficient time until a top layer of oil is formed and partitioned from the remaining aqueous liquid portion. The temperature and time of cold storage depends on the volume of the liquid and the size of the container. When the liquid portion is cold, the oil layer forms; the oil layer is immicible with the aqueous liquid and floats to the top. In general, the temperature is from about −5 to 25° C., preferably about 0-25° C., and more preferably about 0-20° C., 0-15° C., 0-10° C., or 0-5° C. A small fluctuation of temperature, i.e. ±2° C., during the cold storage, is included in this invention. The cooler the temperature, the smaller amount of the liquid, the less time it takes to have the oil layer formed. In general, the liquid portion is stored at a cold temperate for at least one hour, or two hours, or four hours, or 8 hours, or overnight, or 24 hours, or 48 hours, or any range in between the above-recited time. After the cold storage, the oil layer partitions out from the aqueous liquid and floats to the top.

The undesired potentially toxic material, cinnamaldehyde, which is lipid-soluble, is portioned to the top oil layer. The top oil layer is removed carefully by withdrawing or decanting. The toping layer is then discarded. By removing the oil layer, the cinnamaldehyde content in the remaining aqueous liquid is reduced 2-6 fold.

The oil-removal step does not reduce the contents of active ingredients, i.e., polyphenol type-A polymers, because polyphenolic polymers are water-soluble and not lipid-soluble (Anderson et al. *J. Agric. Food Chem.* 52:65-70, 2004). The inventors have discovered that the oil-removal step increases the percent content of polyphenolic polymers in the final product.

After the oil-layer is removed, the remaining aqueous liquid is optionally centrifuged in a tubular centrifuge to remove suspended solids which are between 0.001-1 microns in size. Tubular centrifuges operate at high speed, generating up to 20,000×g, causing liquid to discharge through the outlet and solids to accumulate inside the centrifuge. This tubular centrifugation step is typically carried out at about 14,000-20,000 RPM (about 15,000-17,000×g) at a flow rate of about 20-1200 L/hour, depending on the viscosity of the liquid. This tubular centrifugation step significantly reduces the content of coumarin, which is an undesirable material, in the final product. This tubular centrifugation step also further reduces the content of cinnamaldehyde.

The remaining aqueous liquid can be used directly as an insulin potentiating agent, or the aqueous liquid can be dried to form a powder. The drying can be carried out by any means that can practically dry a large quantity of liquid (over 1 kg, 10 kg, or 100 kg), e.g., lyophilization, spray-drying, or centrifuging and spray-drying. When the optional tubular centrifugation step is omitted in the process, the yield of the dry powder is about 5-20% and often about 8-12% (e.g. about 10%) of the weight of the starting raw material. When the optional tubular centrifugation step is included in the process, the yield of the dry powder is about 3-18% and often about 5-11% of the weight of the starting raw material. The tubular centrifugation step improves the quality of the product, while it may decrease the yield. Depending on the intended use of the final product, the tubular centrifugation step is either included or excluded from the process of this invention.

The process of the present invention improves the water solubility of the product from about 92% to 99%, which is particularly important when the product is used as a beverage. For a beverage, it is desirable to have a minimal amount (≦1%) of insoluble materials. Otherwise, the beverage may not be commercially viable because consumers do not like to taste solids when drinking a beverage.

The liquid or the powder can be incorporated into a variety of basic materials in the form of a liquid, powder, tablets, or capsules to give an insulin potentiating activity effective to decrease blood glucose levels or glycosylated hemoglobin levels. Such a product is effective in lowering blood glucose and glycosylated hemoglobin levels, and is effective in the treatment of hyperglycemia.

EXAMPLES

Example 1

Preparation of Water Extract of Cinnamon 1. 1,200 kg of raw materials of cinnamon bark (*Cinnamomum Cassia*) was divided among 4 tanks, each holding 300 kg of the raw material.
2. Purified water was added into each tank at water to material ratio of 8:1, and the mixture was heated to boil at 100° C. for one hour. The first water extract was removed, and more water was added to the cinnamon solid material at water to material ratio of 6:1; the mixture was boiled at 100° C. for another hour. The second water extract was removed, and more water was added to the cinnamon solid material at water to material ratio of 4:1; the mixture was boiled at 100° C. for another hour. The third water extract was removed.

The water extracts were combined and filtered through a 100-mesh screen to remove solid debris and the filtrates were collected.

3. The filtrates were put into intermediate containers and held static for 4 hours. After static holding, the supernatants were carefully removed and put into a concentration tank for vacuum evaporation to concentrate the filtrates.
4. The vacuum evaporation was performed at 60° C. to 80° C., with vacuum pressure from −0.06 MPa to −0.08 MPa. After 24 hours, a total of 600 L concentrate was obtained.
5. The concentrate was stored in a container at 0-5° C. for 16-24 hours and a top oil layer was formed and separated out from the remaining concentrate. The top oil layer (20-60 L) was removed and discarded.
6. After the top oil layer was removed, the concentrate was optionally centrifuged in a tubular centrifuge (Model GQ 105, Shanghai Centrifuge Institute Co., Ltd.) at 16,000 RPM at about 2 L/minute flow rate. The precipitate was removed and about 500 L of liquid collected. This tubular centrifugation step was optional.
7. The liquid from step 5 or step 6 was then sprayed dry in a high-speed centrifuging and spray-drier (Model: LHS25, Menghe Drying Equipment Works, Jiangsu, China) to form dry powder. The dry powder was mixed and the yield of cinnamon water extract in the dry powder form was about 100-120 kg without step 6, and about 50-110 Kg with step 6, depending on the batch.

Example 2

Comparison of the Contents of Cinnamaldehyde, Coumarin, and Active Ingredients in Products by Three Different Processes Objectives The contents of cinnamaldehyde, coumarin, and active ingredients (polyphenolic polymers, see Anderson et al, J. Agric. Food Chem. 52:65-70, 2004) in the dry powder of water extracts of cinnamon prepared by three different processes were compared.

The water solubility of the dry powder of water extracts of cinnamon prepared by three different processes was also compared.

Process 1 (prior method): dry powder of water extract of cinnamon was prepared by the similar protocols of Example 1, except Step 5 (cold storage and oil removal) and step 6 (centrifugation) were not performed.

Process 2 (invention): dry powder of water extract of cinnamon was prepared by the protocols of Example 1, without the optional step 6 (centrifugation).

Process 3 (invention): dry powder of water extract of cinnamon was prepared by the protocols of Example 1, including the optional step 6 (centrifugation).

Methods

Polyphenolic Polymers and Coumarin

Material Preparation for Testing: 10 mg of dry powder was added to 1 mL of 0.1 N acetic acid. The sample was then centrifuged to remove insoluble and the dry weight of the solution was determined (mg/ml). 0.6 mL of the solution was added to Prep C18 column.

Standards: Coumarin standards were purchased from Sigma Aldrich. The standards of polyphenolic polymers were determined by mass spectroscopy (Anderson et al, 2004).

HPLC Column: 7.8×300 mm Symmetry Prep C18 column, (Waters WAT 066235); 0.1N Acetic acid 92%, 8% acetonitrile for 90 min; gradient to 15% acetonitrile at 130 min; constant to 160 min; gradient to 20% acetonitrile at 180 min; at 200 min, run 8 min gradient to 100% acetonitrile. The absorbance area at 278 nm of each peak was determined and compared with that of a standard. The amount and the identity of the peaks were determined based on the comparison with the standards.

Content Calculation: The amounts of coumarin, and polyphenolic polymers were determined based on the comparison with the standards. Each determined amount was divided by the amount of material added to the column and then converted to percent.

Cinnamaldehyde

Cinnamaldehyde was determined according the method described in Chinese Pharmacopoeia 2005, page 91.

Material Preparation for Testing: 0.5 g of the dry power was weighed. The dry powder was put in a conical flask and 25 ml of methanol was added. The mixture was mixed with an ultrasonic device for 10 minutes (power 350 W, frequency 35 kHz), then stored overnight. The mixture was mixed again with the ultrasonic device for 10 minutes and the weight was measured. Methanol was added to supply the lost weight. The solution was thoroughly mixed and then filtered. Exactly 1 ml of the filtrate was removed, added with 24 mL of methanol, and mixed.

Standard Preparation: Cinnamaldehyde (Sigma Aldrich) was weighed and added with a proper amount of methanol, to prepare the concentration of 10 μg/mL.

HPLC Column: 10 μL of test sample or standard solution was injected into Phenomenex Luna C18 column. The mobile phase was acetonitrile-water (35:75 v/v) and the test wavelength was 290 nm.

Content Calculation: The amount of cinnamaldehyde in the test sample was determined based on the comparison with the standard. The determined amount was divided by the amount of material added to the column and then converted to percent.

Water Solubility 0.1 g of dry powder was added with 100 mL of warm water (about 60° C.), and mixed by an untrasonic device for 30 minutes. The mixture was kept at about 60° C. and filtered through a G3 filter funnel. The filtrate was dried and weighed.

Water-solubility (%)=(1−dry filtrate weight/sample weight)×100%

Results

The results are summarized in Table 1.

TABLE 1

The percent contents of cinnamaldehyde, coumarin, and polyphenolic polymers in the dry powder and the water solubility of the dry powder prepared by three different processes.

| | Cinnamaldehyde Content (%) | Coumarin Content (%) | Polyphenol Polymers Content (%) | Solubility in Water (%) |
|---|---|---|---|---|
| Process 1 (Prior Method) | 0.006 | 0.66 | 3.52 | 91.84 |
| Process 2 (Invention) | 0.001 | 0.60 | 5.20 | 99.19 |
| Process 3 (Invention) | 0.0005 | 0.29 | 4.20 | 99.53 |

The potentially toxic cinnamaldehyde content in the process 1 product (prior art) was 0.006%, and the cinnamaldehyde contents in the process 2 and process 3 products were 0.001 and 0.0005%, respectively. The present processes reduced the cinnamaldehyde content by at least 6-fold.

The potentially toxic coumarin content in the process 1 product (prior art) was 0.66%, and the coumarin contents in the process 2 and process 3 products were 0.60 and 0.29%, respectively. The present process 3 with the centrifugation step reduced the coumarin contents by more than 2 fold; this could be due to the low solubility of coumarin in water.

The polyphenol polymer content in the process 1 product (prior art) was 3.52%, and the polyphenol polymer contents in the process 2 and process 3 products were 5.20 and 4.20%, respectively. The present processes increased the percent content of the active ingredients in the final products.

The present processes 2 and 3 improve the water solubility of the product from about 92% to over 99%, which is particularly important when the product is used as a beverage. For a beverage, it is desirable to have a minimal amount (≦1%) of insoluble materials.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A process for preparing cinnamon water extract, comprising the steps of:
   (a) adding an aqueous solvent to at least 5 Kg of a cinnamon raw material, wherein the ratio of the solvent to the material is 1:1 to 100:1 (w/w),
   (b) boiling the mixture of (a) for at least 5 minutes,
   (c) removing the solid debris from the mixture to obtain a liquid portion,
   (d) concentrating the liquid portion by 5-50 fold,
   (e) storing the concentrated liquid portion at about −5° C. to 25° C. until a top oil layer is formed and partitioned,
   (f) removing the top oil layer, and
   (g) collecting the remaining liquid portion.

2. The process according to claim 1, wherein the aqueous solvent is water.

3. The process according to claim 2, after the step (g), further comprising a step (h) of centrifuging the remaining liquid portion by a tubular centrifuge to remove suspending solids and collecting the supernatant.

4. The process according to claim 3, further comprising a step of drying the supernatant of (h) to obtain the cinnamon water extract in a dry powder form.

5. The process according to claim 2, further comprising a step of drying the liquid portion of (g) to obtain the cinnamon water extract in a dry powder form.

6. The process according to claim 1, wherein the concentrating is performed by vacuum evaporation.

7. The process according to claim 1, further comprising repeating steps (a)-(c) 2-4 times with the same cinnamon raw material, wherein after each boiling step, the liquid portion is removed and collected, and new water is added to the solid material for boiling.

8. The process according to claim 1, wherein the ratio of the solvent to the cinnamon raw material is 2:1 to 50:1 (w/w).

9. The process according to claim 8, wherein the ratio is 10:1 to 30:1 (w/w).

10. The process according to claim 1, wherein the mixture of (a) is boiled for 5 minutes to 10 hours.

11. The process according to claim 10, wherein the mixture of (a) is boiled for 1-4 hours.

12. The process according to claim 1, wherein the concentrated liquid portion of (e) is stored at 0-10° C. for at least 1 hour.

13. The process according to claim 12, wherein the concentrated liquid portion of (e) is stored at 0-10° C. for 4-48 hours.

14. The process according to claim 1, wherein the cinnamon raw material is at least 100 Kg.

15. The process according to claim 14, wherein the cinnamon raw material is at least 1000 Kg.

16. The process according to claim 15, wherein the cinnamon raw material is 100-2000 Kg.

17. The process according to claim 4, wherein the cinnamon raw material is at least 100 Kg, the mixture of (a) is boiled for 1-4 hours, and the concentrated liquid portion of (e) is stored at 0-10° C. for 4-48 hours.

18. The process according to claim 5, wherein the cinnamon raw material is at least 100 Kg, the mixture of (a) is boiled for 1-4 hours, and the concentrated liquid portion of (e) is stored at 0-10° C. for 4-48 hours.

19. The process according to claim 1, wherein the cinnamon raw material is bark from Cinnamomum mairei, Cinnamomum zeylanicum, Cinnamomum burmannii, and Cinnamomum cassia.

* * * * *